United States Patent
Morana et al.

(10) Patent No.: US 11,028,057 B2
(45) Date of Patent: Jun. 8, 2021

(54) PROCESS FOR THE SYNTHESIS OF 6-CHLOROMETHYLURACIL

(71) Applicant: Procos S.P.A., Cameri (IT)

(72) Inventors: Fabio Morana, Novara (IT); Stefano Gobbato, Cameri (IT); Jacopo Roletto, Turin (IT); Paolo Paissoni, Druento (IT)

(73) Assignee: Procos S.P.A., Cameri (IT)

( * ) Notice: Subject to any disclaimer, the term of this patent is extended or adjusted under 35 U.S.C. 154(b) by 0 days.

(21) Appl. No.: 16/975,800

(22) PCT Filed: Feb. 13, 2019

(86) PCT No.: PCT/IB2019/051155
§ 371 (c)(1),
(2) Date: Aug. 26, 2020

(87) PCT Pub. No.: WO2019/166901
PCT Pub. Date: Sep. 6, 2019

(65) Prior Publication Data
US 2020/0407330 A1    Dec. 31, 2020

(30) Foreign Application Priority Data
Feb. 28, 2018   (IT) .................. 102018000003134

(51) Int. Cl.
*C07D 239/54* (2006.01)

(52) U.S. Cl.
CPC ................. *C07D 239/54* (2013.01)

(58) Field of Classification Search
CPC ................................... C07D 239/54
See application file for complete search history.

(56) References Cited

PUBLICATIONS

Bazazan, Heterocycl COmmunications, vol. 19(6), 401-404, 2013. (Year: 2013).*

Mojtahedi, Synthetic Communicaitons, vol. 32(6), 851-855, 2002. (Year: 2002).*

Feb. 13, 2019 Reply to Search Opinion Established by the European Patent Office for priority Italian Application No. 102018000003134 filed Feb. 28, 2018.

Botta M. et al., "Synthesis and biological evaluation of 2-methoxy- and 2-methylthio-6-[(2'-alkylamino)ethyl]-4(3H)-pyrimidinones with anti-rubella virus activity", Bioorganic & Medicinal Chemistry, Pergamon, GB, vol. 7, No. 9, Sep. 1, 1999, pp. 1925-1931.

Janietz D. et al., "Chloromethyl-substituierte heterocyclen aus chlortetrolsauremethylester, Chloromethyl substituted heterocycles from methyl chlorotetrolated", Journal Fur Praktische Chemie: Practical Applications and Applied Chemistry: Covering all aspetct of Applied Chemistry, Wiley, DE vol. 330, No. 4, Jan. 1, 1988, pp. 607-616.

Search Report and Written Opinion of PCT/IB2019/051155 dated May 16, 2019.

* cited by examiner

*Primary Examiner* — D Margaret M Seaman

(74) *Attorney, Agent, or Firm* — Silvia Salvadori, P.C.; Silvia Salvadori

(57) ABSTRACT

The invention relates to a process for the synthesis of 6-chloromethyluracil (6-(chloromethyl)pyrimidin-2,4(1H,3H)-dione) from ethyl 4-chloroacetoacetate and S-methylisothiourea hemisulfate via isolation of the novel intermediate 6-(chloromethyl)-6-hydroxy-2-(methylthio)-5,6-dihydropyrimidin-4(1H)-one, and its subsequent treatment with aqueous sulfuric acid. Formula (I).

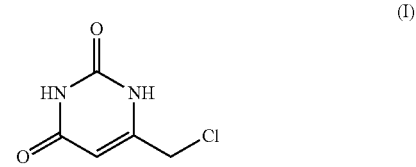

(I)

7 Claims, No Drawings

PROCESS FOR THE SYNTHESIS OF 6-CHLOROMETHYLURACIL

This application is a U.S. national stage of PCT/IB2019/051155 filed on 13 Feb. 2019, which claims priority to and the benefit of Italian Application No. 102018000003134 filed on 28 Feb. 2018, the contents of which are incorporated herein by reference in their entireties.

TECHNICAL FIELD OF INVENTION

The invention relates to a process for the synthesis of 6-chloromethyluracil (6-(chloromethyl)pyrimidin-2,4(1H,3H)-dione) from ethyl 4-chloroacetoacetate and S-methylisothiourea hemisulfate via isolation of the novel intermediate 6-(chloromethyl)-6-hydroxy-2-(methylthio)-5,6-dihydropyrimidin-4(1H)-one, and its subsequent treatment with aqueous sulfuric acid.

BACKGROUND TO THE INVENTION

6-Chloromethyluracil is a key intermediate in the synthesis of thymidine phosphorylase inhibitors, including tipiracil. The latter, in combination with trifluridine, is an active ingredient used in a proprietary medicament for the treatment of metastatic colorectal cancer.

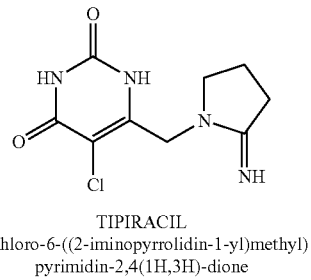

TIPIRACIL
5-chloro-6-((2-iminopyrrolidin-1-yl)methyl)pyrimidin-2,4(1H,3H)-dione

Various preparations of 6-chloromethyluracil are reported in the literature:

*Heterocycl. Commun.* 2013, 19(6), 401-404 reports hot condensation of ethyl 4-chloroacetoacetate and urea in the presence of polyphosphoric acid (PPA)

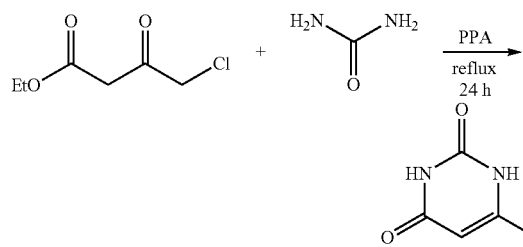

In view of the low reactivity of one of the two reagents, urea, said procedure requires extremely drastic conditions (use of inorganic acids as undiluted solvents, long reaction times and very high temperatures). Moreover, the authors refer to the product as a "brown powder", a description that implies its low purity since, when pure, it is a white crystalline solid.

*Synthetic Communications* 2002, 32(6), 851-855 reports the same condensation in the absence of acid, promoted by the use of microwaves. Said procedure has the drawback of not being industrially feasible due to the use of microwaves.

*J. Am. Chem. Soc.* 1914, 36 (8), 1742-1747 describes the synthesis in 4 steps, starting from ethyl chloroacetate and sodium ethoxide, initially giving ethoxyacetic acid ethyl ester; the latter is condensed with ethyl bromoacetate in the presence of zinc amalgam to give ethyl 4-ethoxyacetoacetate which, by reaction with thiourea and subsequent hot hydrolysis in aqueous hydrochloric acid, yields the desired product.

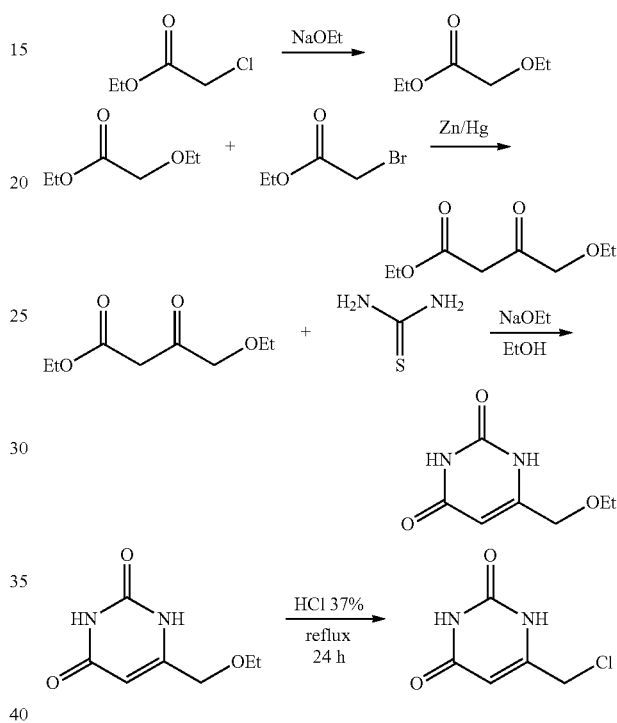

The length of the synthesis and the use of zinc amalgam (which is highly toxic) makes this method unattractive for industrial scale-up.

*Nucleosides, Nucleotides, and Nucleic Acids* 2005, 24 (5-7):367-373 and *Eur. J. Med. Chem.* 2013, 70, 400-410 describes a sequence starting with oxidation of 6-methyluracil to uracil-6-carbaldehyde in the presence of selenium dioxide, followed by reduction with sodium borohydride and chlorination with thionyl chloride.

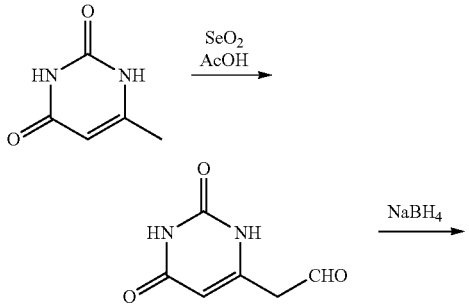

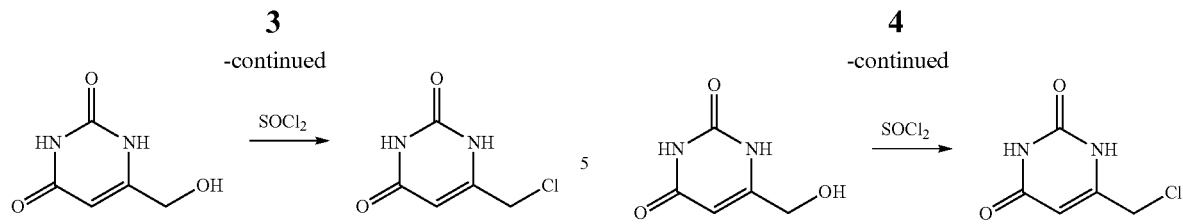

Once again, the length of the synthesis and the use of highly toxic elements like selenium means that the procedure is of little industrial interest.

CN106892902A discloses the same sequence, except that the first oxidation to aldehyde is effected in the presence of copper oxide (CuO). The length of the synthesis and the use of transition metals that may contaminate the end product means that this procedure is of no industrial interest.

CN105906573A discloses a process starting with identical oxidation of 6-methyluracil to uracil-6-carbaldehyde, followed by iodination, reduction to alcohol, chlorination, and removal of iodine with butyllithium.

The considerable cost of the raw material, the number of steps and the use of a toxic substance in the step that gives rise to the product make this procedure very unattractive.

*Journal fuer Praktische Chemie* (*Leipzig*) 1988, 330(4), 607-16 reports two-step synthesis starting with methyl 4-clorobut-2-inoate and S-methylisothiourea, via isolation of intermediate 6-(chloromethyl)-2-(methylthio)pyrimidin-4(1H)-one.

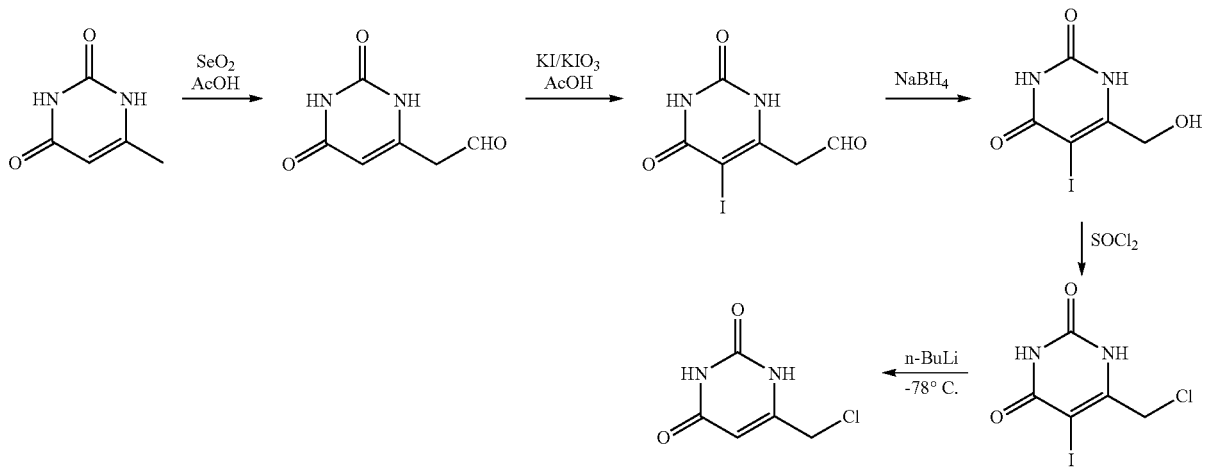

Said procedure has numerous obvious disadvantages, such as the large number of steps, the use of toxic substances such as selenium, the use of oxidants such as potassium iodate, and the drastic reaction conditions of the final step, which are required to manage an organometallic reagent safely, and incompatible with industrial processes.

CN104725324A and CN106831607 disclose the esterification of orotic acid, followed by reduction and chlorination.

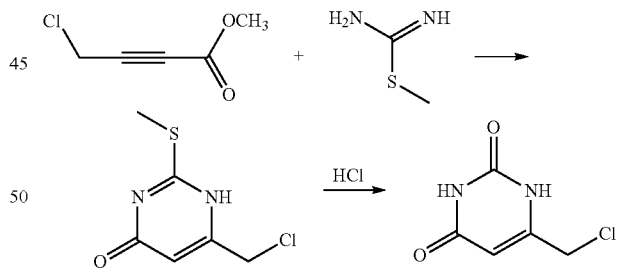

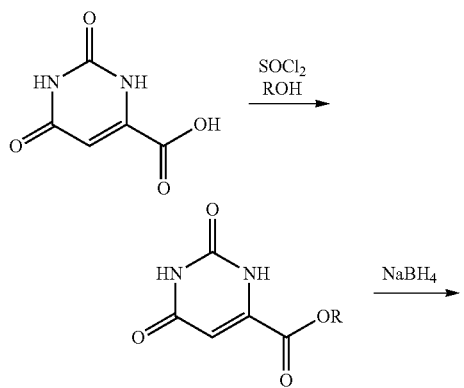

Said procedure seems disadvantageous due to the low commercial availability of the starting alkyne, for whose synthesis additional steps would be required, which means that the quality and yield of the alkyne are unknown.

Moreover, the first step is effected by reacting the two raw materials in a strongly basic medium at 70° C. However, it is known that S-methylisothiourea (and the salts thereof) already degrade at room temperature in the presence of sodium hydroxide, releasing gaseous methanethiol. Said procedure is used to indirectly generate methanethiol as a reagent in processes that require its use, as it is a toxic, foul-smelling, extremely volatile gas. See, for example, the article "Ex Situ Formation of Methanethiol: Application in the Gold(I)-Promoted Anti-Markovnikov Hydrothiolation of Olefins" *Angew. Chem. Int. Ed.,* 2018, 57 (42) 13887-13891.

The problems of operator safety and environmental safety due to uncontrolled release of methanethiol would in this case be accompanied by chemical problems, because the gas performs a nucleophilic substitution on the chlorine atom, leading to the by-product 6-((methylthio)methyl)pyrimidin-2,4(1H,3H)-dione, as discussed below and shown in Scheme 2.

The formation of said by-product is particularly promoted in the second step, because aqueous hydrochloric acid is used to hydrolyse the thiomethyl group on the ring; the solubility of methanethiol in said aqueous acid is very high, and the gas retained in solution is wholly incorporated in the molecule, leading to further formation of 6-((methylthio)methyl)pyrimidin-2,4(1H,3H)-dione, with a loss of yield of the end product 6-chloromethyluracil and almost impossible purification using easily industrialisable methods such as crystallisation.

The synthesis of 6-(chloromethyl)-2-(methylthio)pyrimidin-4(1H)-one is also described in WO2007080382A1, WO2008023180A1, WO2009007749A2, WO2004063156, CN103980253A, *Bioorg. Med. Chem. Lett.* 2012, 22, 4163-4168 and *Bioorg. Med. Chem.* 1999, 7, 1925-1931, which report the isolation of the compound from ethyl 4-chloroacetoacetate and S-methylisothiourea hemisulfate. In these cases the product is sometimes reported in its tautomeric form 6-(chloromethyl)-2-(methylthio)pyrimidin-4-ol, as shown in the scheme below.

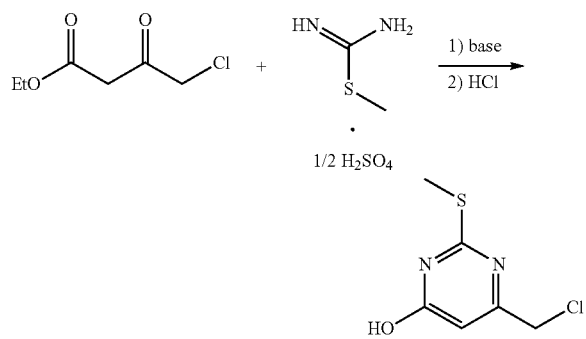

In such procedures, the molecule is isolated by filtration after the reaction has been effected at 25° C. It is also expressly recommended that the filtration mother liquor should be acidified to obtain another precipitate and increase the yield of the desired product. In *Bioorg. Med. Chem.* 1999, 7, 1925-1931 the product is isolated by neutralising the reaction mixture with hydrochloric acid, followed by extraction and column chromatography.

In practice, these operations involve obvious disadvantages.

Carrying out the reaction at 25° C. accelerates the partial degradation of one of the two reagents, ethyl 4-chloroacetoacetate, which is unstable at basic pH values due to the presence of inorganic bases such as carbonates or as calcium hydroxide used in *Bioorg. Med. Chem.* 1999, 7, 1925-19. Said degradation competes with the reactivity of the molecule to give the desired product, therefore adversely affecting its yield and purity.

At room temperature, the presence of numerous inorganic saline species, released by one of the two reagents, present in the form of hemisulfate, and by the inorganic base used, promotes the uncontrolled release of gaseous methyl mercaptan from the desired product, which therefore partly evolves to 6-chloromethyluracil.

This uncontrolled development of gas is accelerated by adding HCl to the filtration mother liquor. The resulting precipitate is usually a mixture of three products: the desired product, 6-chloromethyluracil, and 6-((methylthio)methyl)pyrimidin-2,4(1H,3H)-dione, since hydrochloric acid not only promotes the release of methyl mercaptan, but also its residence in solution to replace the terminal chlorine atom by nucleophilic substitution, as shown in Scheme 2 below.

Demonstrating the multiplicity of by-products generated by this procedure, *Bioorg. Med. Chem.* 1999, 7, 1925-1931 expressly states (p. 1930) that the product was "purified" by column chromatography, without specifying the degree of purity of the product obtained. Moreover, the need for chromatographic purification prevents this procedure from being industrially scalable.

CN103980253A discloses the hydrolysis of 5-chloro-6-(chloromethyl)-2-(methylthio)pyrimidin-4(1H)-one to 5-chloro-6-chloromethylpyrimidin-2,4(1H,3H)-dione with a solution of 6M hydrochloric acid or 2M sulfuric acid.

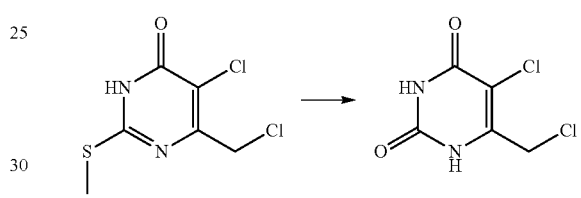

*Yakugaku Zasshi,* 1950, 70, 134-137 describes the hot hydrolysis of 6-methyl-2-methylthiopyrimidin-4(1H)-one to 6-methylpyrimidin-2,4(1H,3H)-dione with sulfuric acid.

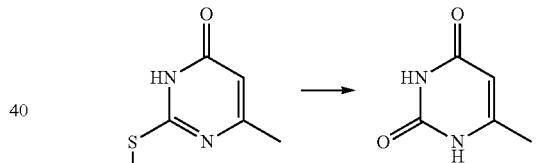

DESCRIPTION OF THE INVENTION

The object of the present invention is a process for the preparation of 6-chloromethyluracil comprising the following steps:

a) reacting ethyl 4-chloroacetoacetate and S-methylisothiourea hemisulfate to give the isolated intermediate 6-(chloromethyl)-6-hydroxy-2-(methylthio)-5,6-dihydropyrimidin-4(1H)-one;

b) reacting said 6-(chloromethyl)-6-hydroxy-2-(methylthio)-5,6-dihydropyrimidin-4(1H)-one with aqueous sulfuric acid to give 6-chloromethyluracil.

The intermediate 6-(chloromethyl)-6-hydroxy-2-(methylthio)-5,6-dihydropyrimidin-4(1H)-one is novel, and is a further object of the invention.

The process according to the invention therefore consists of two steps (Scheme 1), which involve:

a) Obtaining and isolating the novel intermediate 6-(chloromethyl)-6-hydroxy-2-(methylthio)-5,6-dihydropyrimidin-4(1H)-one from ethyl 4-chloroacetoacetate and S-methylisothiourea hemisulfate, preferably at low temperatures. Isolation of the intermediate allows the removal of numerous inorganic saline species, which make the subsequent hydrolysis step, to form the uracil scaffold, particularly liable to variability in the hydrolysis rate, with release of methyl mercaptan (a toxic gas), and consequent poor control of gas development. Said problems are those usually encountered in isolation at room temperature of 6-(chloromethyl)-2-(methylthio)pyrimidin-4(1H)-one starting with the same raw materials, ethyl 4-chloroacetoacetate and S-methylisothiourea, as illustrated in the background to the invention and in Scheme 2.

b) Treating the isolated intermediate 6-(chloromethyl)-6-hydroxy-2-(methylthio)-5,6-dihydropyrimidin-4(1H)-one with aqueous sulfuric acid to give 6-chloromethyluracil via generation in situ of the intermediate 6-(chloromethyl)-2-(methylthio)pyrimidin-4(1H)-one. Said treatment presents a multiplicity of surprising advantages over the already known use of hydrochloric acid to convert isolated 6-(chloromethyl)-2-(methylthio)pyrimidin-4(1H)-one to 6-chloromethyluracil. The use of sulfuric acid reduces the amount of the by-product 6-((methylthio)methyl)pyrimidin-2,4(1H,3H)-dione to under 0.5%, with a very favourable impact on the yield and quality of the end product. It is therefore unnecessary to subject the resulting 6-chloromethyluracil to further purification steps. Moreover, the use of sulfuric acid leads to total conversion of the reaction in much shorter times.

All of said arguments offer obvious advantages for the purpose of optimising the occupation of industrial facilities.

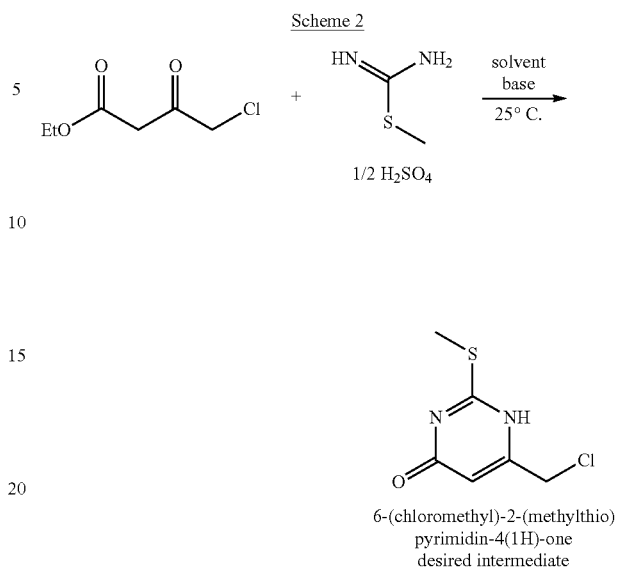

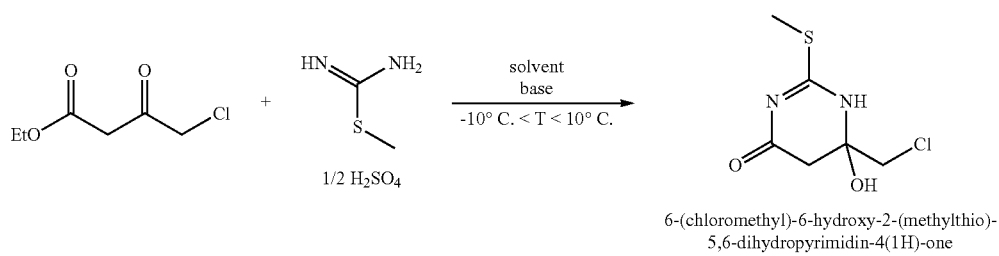

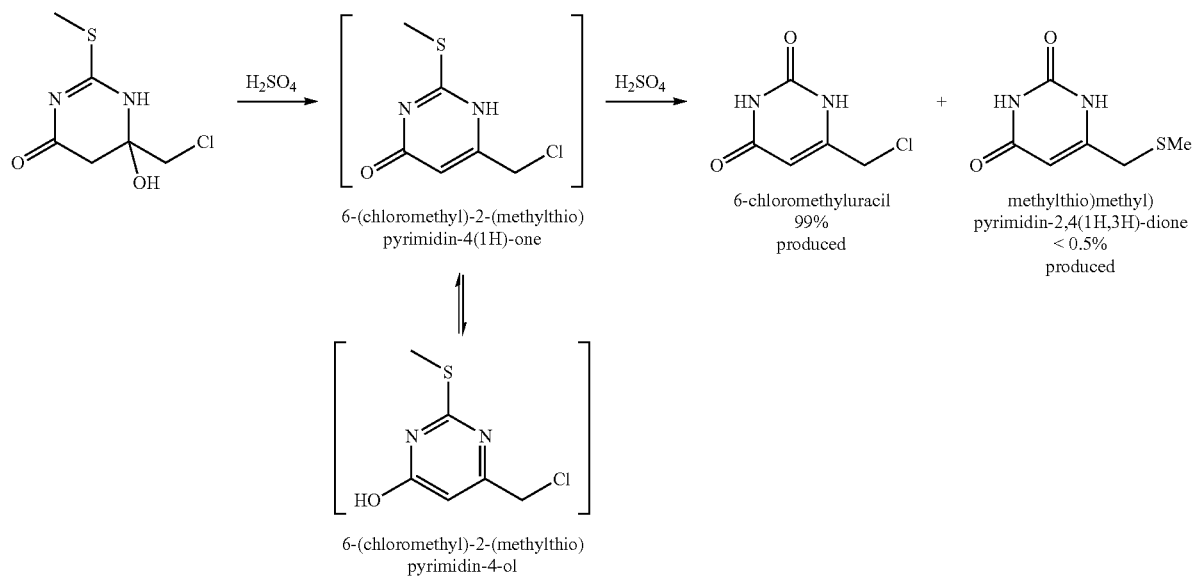

-continued

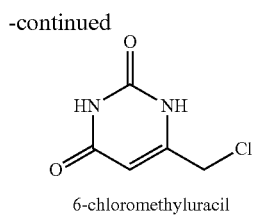

6-chloromethyluracil
formed by the uncontrolled release of MeSH
at 25° C. in the presence of inorganic saline species

+

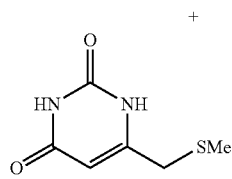

6-((methylthio)methyl)pyrimidin-2,4(1H,3H)-dione
by-product of incorporation of MeSH at 25° C.
in the presence of inorganic saline species

DETAILED DESCRIPTION OF THE INVENTION

The order of addition of the solvents, raw materials, acids or bases may differ from that reported below.

In one embodiment of the invention, the process is effected as follows:

Step a): 1 molar equivalent of ethyl 4-chloroacetoacetate is reacted with 1-2 molar equivalents of S-methylisothiourea hemisulfate, preferably 1.1-1.5 molar equivalents, in the presence of 1-2 molar equivalents of an inorganic base, preferably 1.1-1.5 molar equivalents, selected from sodium carbonate, potassium carbonate, sodium bicarbonate, potassium bicarbonate, preferably sodium carbonate, in 3-30 volumes, preferably 5-10 volumes, of water or an organic solvent selected from water, methanol, acetonitrile, ethanol, acetone, N,N-dimethylformamide and N,N-dimethylacetamide, preferably water, at a temperature ranging between −10 and +10° C., preferably between −5 and +5° C. The progress of the reaction is monitored by UPLC/MS analysis using an ACQUITY UPLC® BEH column, C18, 17 µm, 2.1×50 mm, and water/acetonitrile/0.1% formic acid as eluent phase. When the reaction is complete, the resulting suspension is filtered and the solid is dried under vacuum at a temperature of 30-90° C., preferably 40-60° C., exhibiting a purity exceeding 99%.

Step b): 1 molar equivalent of the 6-(chloromethyl)-6-hydroxy-2-(methylthio)-5,6-dihydropyrimidin-4(1H)-one obtained in step a) is suspended in aqueous sulfuric acid 0.1-20% by weight, preferably 1-10% by weight, 2-30 volumes, preferably 4-8 volumes, at a temperature of 40-120° C., preferably 70-100° C. The progress of the reaction is monitored by UPLC/MS analysis using an ACQUITY UPLC® BEH column, C18, 17 µm, 2.1×50 mm, and water/acetonitrile/0.1% formic acid as eluent phase. When the reaction is complete, the mixture is cooled to −3-30° C., preferably 0-10° C., and the resulting suspension is filtered. The solid is dried under vacuum at a temperature of 30-90° C., preferably 40-60° C., exhibiting a purity exceeding 99%.

In a particular embodiment of step b), it is initially effected at a temperature of 0-40° C., preferably 25° C., under which conditions 6-(chloromethyl)-6-hydroxy-2-(methylthio)-5,6-dihydropyrimidin-4(1H)-one is converted in situ to the intermediate 6-chloromethyl-2-(methylthio)pyrimidin-4(1H)-one, or its tautomeric form 6-(chloromethyl)-2-(methylthio)pyrimidin-4-ol (Scheme 1), which are subsequently converted to 6-chloromethyluracil by heating at 40-120° C.

The invention is illustrated in detail in the following examples.

Example 1

S-Methylisothiourea hemisulfate (1.20 equivalents, 20.3 g, 145.8 mmol) is dissolved in 120 mL of water, and the solution is stirred for 10 minutes at 20° C. in a nitrogen atmosphere. Sodium carbonate (1.15 equivalents, 14.8 g, 139.7 mmol) is then added to the solution, and the mixture is stirred at 20° C. for 30 minutes. After this time, the mixture is cooled to −5° C., and ethyl 4-chloroacetoacetate (1.0 equivalents, 20 g, 121.5 mmol) is added to the reaction mixture in 1 h. When the addition is complete, the mixture is stirred for 1 h at −5° C., and then filtered. The resulting white solid is dried under vacuum at 50° C. for 20 h. The intermediate 6-(chloromethyl)-6-hydroxy-2-(methylthio)-5,6-dihydropyrimidin-4(1H)-one is obtained with a yield of 60% (15.2 g) and purity >99%.

[M+H]$^+$ 209 m/z
[M−H]$^−$ 207 m/z
$^1$H-NMR (d$_6$-DMSO, the chemical shifts expressed in ppm relate to the TMS signal):
2.33 (3H, s), 2.47 (1H diastereotopic CH$_2$, d, J=16.8 Hz), 2.67 (1H diastereotopic CH$_2$, d, J=16.8 Hz), 3.61 (2H, s), 6.05 (1H, OH), 10.89 (1H, NH).
$^{13}$C-NMR (d$_6$-DMSO): 13.3, 39.7, 52.7, 84.8, 156.2, 169.2.

Example 2

6-(Chloromethyl)-6-hydroxy-2-(methylthio)-5,6-dihydropyrimidin-4(1H)-one (15 g, 71.9 mmol) is suspended in 75 mL of an aqueous solution of 5% aqueous sulfuric acid by weight, and the mixture is heated to 80° C. in a nitrogen atmosphere for 30 minutes. When the reaction is complete, the mixture is cooled to 5° C. and stirred at said temperature for 1 h before filtration. The resulting white solid is dried under vacuum at 50° C. for 20 h. The end product 6-chloromethyluracil is obtained with a yield of 90% (10.4 g) and purity >99%. The amount of the by-product 6-((methylthio)methyl)pyrimidin-2,4(1H,3H)-dione (product deriving from nucleophilic substitution of methyl mercaptan released from the reaction on the chlorine atom) present in the crystal of the desired product is 0.42%.

[M−H]$^−$ 159 m/z
$^1$H-NMR (d$_6$-DMSO, the chemical shifts expressed in ppm relate to the TMS signal):
4.38 (2H, s), 5.67 (1H, s), 11.11 (2H, NH).
$^{13}$C-NMR (d$_6$-DMSO): 41.5, 101.1, 151.8, 152.3, 164.8.

Example 3

6-(Chloromethyl)-6-hydroxy-2-(methylthio)-5,6-dihydropyrimidin-4(1H)-one (20 g, 95.9 mmol) is suspended in 100 mL of an aqueous solution of 5% aqueous sulfuric acid by weight, and the mixture is stirred at 25° C. in a nitrogen atmosphere for 1 h to obtain complete conversion to 6-(chloromethyl)-2-(methylthio)pyrimidin-4(1H)-one (from UPLC-MS and HPLC analysis). The mixture is then heated at 80° C. for 30 minutes. When the reaction has terminated, the mixture is cooled to 5° C. and stirred at said temperature for 1 h before filtration. The resulting white solid is dried under vacuum at 50° C. for 20 h. The end product 6-chloromethyluracil is obtained with a yield of 88% (13.6 g) and purity >99%. The amount of the by-product 6-((methylthio)methyl)pyrimidin-2,4(1H,3H)-dione (product deriving from nucleophilic substitution of methyl mercaptan released from the reaction on the chlorine atom) present in the crystal of the desired product is 0.45%.

The product analysis data are identical to those set out in Example 2.

Comparative Example 1

6-(Chloromethyl)-6-hydroxy-2-(methylthio)-5,6-dihydropyrimidin-4(1H)-one (15 g, 71.9 mmol) is suspended in 75 mL of an aqueous solution of 6N hydrochloric acid, and the mixture is heated to 100° C. in a nitrogen atmosphere for 16 hours. When the reaction has terminated, the mixture is cooled to 5° C. and stirred at said temperature for 1 h before filtration. The resulting white/pale yellow solid is dried under vacuum at 50° C. for 20 h. The end product 6-chloromethyluracil is obtained with a yield of 60% (10.4 g) and purity of 85%. The amount of the by-product 6-((methylthio)methyl)pyrimidin-2,4(1H,3H)-dione (product deriving from nucleophilic substitution of methyl mercaptan released from the reaction on the chlorine atom) present in the crystal of the desired product is 8.5%.

The invention claimed is:

1. A process for the preparation of 6-chloromethyluracil comprising the following steps:
   a) reacting ethyl 4-chloroacetoacetate and S-methylisothiourea hemisulfate to yield the isolated intermediate 6-(chloromethyl)-6-hydroxy-2-(methylthio)-5,6-dihydropyrimidin-4(1H)-one;
   b) reacting said 6-(chloromethyl)-6-hydroxy-2-(methylthio)-5,6-dihydropyrimidin-4(1H)-one with aqueous sulfuric acid to yield 6-chloromethyluracil.

2. The process according to claim 1, wherein step a) is carried out in the presence of an inorganic base at a temperature ranging between −10° C. and 10° C.

3. The process according to claim 2, wherein the inorganic base is selected from sodium carbonate, potassium carbonate, sodium bicarbonate and potassium bicarbonate.

4. The process according to claim 3, wherein the inorganic base is sodium carbonate.

5. The process according to claim 1, wherein step b) is carried out at a temperature of 40-120° C.

6. The process according to claim 1, wherein step b) involves in situ conversion of 6-(chloromethyl)-6-hydroxy-2-(methylthio)-5,6-dihydropyrimidin-4(1H)-one to the intermediate 6-chloromethyl-2-(methylthio)pyrimidin-4(1H)-one or its tautomeric form 6-(chloromethyl)-2-(methylthio)pyrimidin-4-ol, which are then converted to 6-chloromethyluracil.

7. The compound 6-(chloromethyl)-6-hydroxy-2-(methylthio)-5,6-dihydropyrimidin-4(1H)-one.

* * * * *